United States Patent [19]

Botta et al.

[11] Patent Number: 5,338,861
[45] Date of Patent: Aug. 16, 1994

[54] PROCESS FOR THE PREPARATION OF N-SUBSTITUTED LACTAMS

[75] Inventors: Artur Botta; Hans-Josef Buysch; Otto Immel, all of Krefeld; Lothar Puppe, Burscheid, all of Fed. Rep. of Germany

[73] Assignee: Bayer Aktiengesellschaft, Leverkusen, Fed. Rep. of Germany

[21] Appl. No.: 919,818

[22] Filed: Jul. 24, 1992

[30] Foreign Application Priority Data

Aug. 1, 1991 [DE] Fed. Rep. of Germany ........ 4125457

[51] Int. Cl.$^5$ ................ C07D 215/22; C07D 213/64; C07D 201/04; C07D 207/267
[52] U.S. Cl. .................................. 548/552; 548/427; 548/472; 548/952; 546/101; 546/154; 546/290; 540/451; 540/470; 540/485; 540/476
[58] Field of Search ............... 548/552, 427, 472, 952; 546/101, 154, 290; 540/451, 470, 476, 485

[56] References Cited

FOREIGN PATENT DOCUMENTS 5159090 11/1990 Australia .

OTHER PUBLICATIONS

CA86(22):161290k, "Vehicle compositon containing 1-substituted azacyloheptan . . . ", Chem. Abstr. 16 Feb. 1987 p. 18.
CA99(3):±8122v, "Plant pest control", Chem. Abstr. 16 Feb. 1987, p. 10.
CA81(18):106237v, "N-Alkyllactams", Chem. Abstr. 16 Feb. 1987, p. 21.
H. Glaser, Stickstoff-verbindungen II, 1957, pp. 948–952.
Klaus Wehner, "Entwicklung eines technischen Verfahrens zur Herstellung von N-Methyl-ε-caprolactam," Apr. 1981, p. 196.

*Primary Examiner*—David B. Springer
*Attorney, Agent, or Firm*—Sprung Horn Kramer & Woods

[57] ABSTRACT

Substituted lactams of the formula

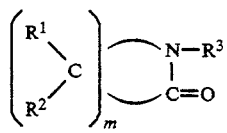

(I)

can be prepared from lactam N-carboxylates or lactim O-carboxylates of the formulae

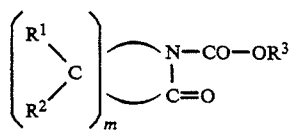

(II)

or

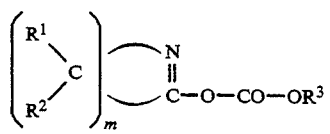

(III)

by thermal or mixed thermal and catalysed $CO_2$ elimination at 80°–450° C. Lactams substituted on the N atom by aliphatic groups such as those produced herein are useful as industrial aprotic solvents.

16 Claims, No Drawings

PROCESS FOR THE PREPARATION OF N-SUBSTITUTED LACTAMS

BACKGROUND OF THE INVENTION

Field of the Invention

The invention relates to a process for the preparation of lactams which are N-substituted by aliphatic radicals by reaction of appropriately substituted lactam N-carboxylates or lactim O-carboxylates at elevated temperature and if appropriate in the presence of catalysts. The necessary lactam N-carboxylates or lactim O-carboxylates can be prepared in situ from lactams which are unsubstituted on the nitrogen and aliphatic carbonates or pyrocarbonates and are immediately further converted to the N-substituted lactams without intermediate isolation.

Lactams substituted on the N atom by aliphatic groups, such as N-methyl-pyrrolidone (NMP) or N-methyl-caprolactam (NMC), are important industrial aprotic solvents, especially for extractions and extractive distillations; they can also be employed as basic compounds for the deacidification of natural gas or industrial gases (Chem. Techn [Leipzig], 33 (4) (1981), 193–196).

Description of the Related Art

For the preparation of N-alkyl-lactams, it is known to react lactams unsubstituted on the nitrogen in the free form or in the alkali metal salt form with alkylating agents, such as alkyl halides or dialkyl sulphates (Houben-Weyl, Methoden der organischen Chemie, [Methods of organic chemistry], Stickstoffverbindungen II and III [Nitrogen compounds II and III] Vol. XI/2, p. 569). A further summary of the prior art for the alkylation of caprolactam is found in the above literature reference Chem. Techn. (loc. cit.). In this publication, the development of an industrial process for the preparation of N-methylcaprolactam is furthermore reported which is characterised by reaction of caprolactamin the gas phase on alumina contact catalysts using 3 mol of methanol as the alkylating agent; the selectivity is 90% in this case, but the conversion is only 65%. Gaseous or low-boiling, foul-smelling, amine-like cleavage products are formed in this process, which have to be disposed of together with the resulting process water in a costly manner (DD 226,563).

SUMMARY OF THE INVENTION

A process has now been found for the preparation of N-substituted lactams of the formula

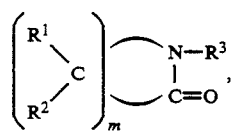
(I)

in which
 m denotes an integer from 2 to 12,
 $R^1$ and $R^2$ independently of one another represent hydrogen, straight-chain or branched $C_1$–$C_6$-alkyl, straight-chain or branched $C_3$–$C_6$-alkenyl, $C_5$–$C_7$-cycloalkyl, benzyl, phenyl, fluorine, chlorine or bromine, at most four substituents $R^1$ and $R^2$ other than hydrogen being present on the number of C ring men, hers designated by the index m and it furthermore being possible to replace one or two of the C ring members in brackets by —N(CH$_3$)— or —N(C$_2$H$_5$)—, it being possible to link several of these C ring members by double bonds or it being possible for two or more of the C ring members in brackets to be parts of a further aromatic or cycloaliphatic ring, and the radicals $R^1$ and $R^2$ representing the supplementary parts of such a ring, and
 $R^3$ denotes straight-chain or branched $C_1$–$C_8$-alkyl, $C_3$–$C_8$-alkenyl or $C_3$–$C_8$-alkinyl or $C_5$–$C_7$-cycloalkyl, which is characterised in that lactam N-carboxylates or lactim O-carboxylates of the formulae

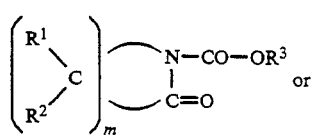
(II)

or

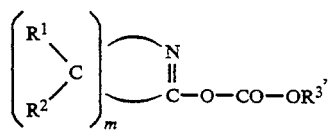
(III)

in which m, $R^1$, $R^2$ and $R^3$ have the above meaning, are cleaved, with elimination of $CO_2$, at temperatures of 80°–450° C. in the gas or the liquid phase and in the presence or absence of catalysts having acidic and/or basic centers and in the presence or absence of an inert solvent, in the case of the use of lactim O-carboxylates the intermediately formed lactim ethers being rearranged under the reaction conditions to the N-substituted lactams.

DETAILED DESCRIPTION OF THE INVENTION

Straight-chain or branched $C_1$–$C_8$-alkyl is, for example, methyl, ethyl, propyl, isopropyl, butyl, isobutyl, the isomeric pentyls, hexyls or octyls. Preferred alkyl has 1–4 C atoms and is particularly preferably methyl or ethyl.

Straight-chain or branched $C_3$–$C_6$-alkenyl is, for example, propenyl, allyl, butenyl, pentenyl or hexenyl. Alkenyl is preferably allyl or butenyl.

Straight-chain or branched $C_3$–$C_8$-alkinyl is, for example, propargyl, butinyl, pentinyl, hexinyl or octinyl, preferably propargyl.

$C_5$–$C_7$-cycloalkyl is, for example, cyclopentyl, methylcyclopentyl, cyclohexyl, methyl-cyclohexyl or cycloheptyl, preferably cyclopentyl or cyclohexyl.

The index m denotes integers from 2 to 12 and thus defines lactam structures having 4–14 ring members. Preferentially, the index m denotes the numbers 3, 4, 5 or 12.

Lactam N-carboxylates or lactim O-carboxylates of the formulae (II) or (III) can be prepared by reaction of lactams with chloroformates in the presence of tertiary amines or by reaction of lactim ethers with chloroformates (German Offenlegungsschrift 1,670,790; German Offenlegungsschrift 1,670,850; German Offenlegungsschrift 1,670,851; German Patentsschrift 949,057).

In a preferred variant according to the invention, however, the lactam N-carboxylates and lactim O-carboxylates mentioned can also be prepared in situ from the lactams which are unsubstituted on the nitrogen and aliphatic carbonates or pyrocarbonates and further converted, without it being necessary to isolate them, to the N-substituted lactams of the formula (I) with elimination of $CO_2$.

The invention therefore relates in this preferred variant to a process for the preparation of N-substituted lactams of the formula (I), which is characterised in that the lactam N-carboxylates and lactim O-carboxylates to be employed are prepared in situ by-reaction of lactams of the formula

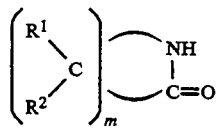  (IV)

with carbonates or pyrocarbonates of the formula

  (V), in which m, $R^1$, $R^2$ and $R^3$ have the abovementioned meaning, and n denotes 0 or 1, in an amount of 0.5–5 mol, preferably 1–3 mol, particularly preferably 1.2–1.7 mol of carbonate or pyrocarbonate per mol of lactam, at temperatures of 80°–450° C. in the gas or the liquid phase and in the presence or absence of catalysts having acidic and/or basic centers and in the presence or absence of an inert solvent, and are converted into the N-substituted lactams under the same conditions and with $CO_2$ elimination without intermediate isolation.

In terms of formulae, the course of the process according to the invention including the preferred variants can be represented as follows as exemplified by the preparation of NMC:

ately formed are not stable; they are rather converted in situ with $CO_2$ elimination into the desired N-substituted lactams. The rearrangement of the lactim ether to the N-substituted lactam is known.

Preferentially, lactam structures according to the invention are taken to mean those in which $R^1$ and $R^2$ are replaced by $R^{11}$ and $R^{12}$, where $R^{11}$ denotes hydrogen, straight-chain or branched $C_1$–$C_4$-alkyl, allyl, butenyl, $C_5$–$C_7$-cycloalkyl, benzyl, phenyl or chlorine and represents hydrogen, straight-chain or branched $C_1$–$C_4$-alkyl or chlorine.

Particularly preferentially, lactam structures according to the invention are taken to mean those in which $R^{11}$ and $R^{12}$ are replaced by $R^{21}$ and $R^{22}$, where $R^{21}$ denotes hydrogen, methyl, ethyl, benzyl or phenyl and $R^{22}$ represents hydrogen, methyl or ethyl.

The radicals $R^1$ and $R^2$ or $R^{11}$ and $R^{12}$ or $R^{21}$ and $R^{22}$ are present in the lactam structures at most four times, independently of their ring size, if they represent substituents other than hydrogen. Preferentially, substituents of the type mentioned other than hydrogen are present at most twice. The substituents mentioned, which are present at most four times, preferably at most twice, can reside on the same C atom and on different C atoms of the lactam structure.

In a furthermore preferred manner, N-substituted lactams are prepared in which $R^3$ is replaced by $R^{13}$ having the meaning straight-chain or branched $C_1$–$C_4$-alkyl, allyl or propargyl. In a particularly preferred manner, N-substituted lactams are prepared in which $R^{13}$ is replaced by $R^{23}$ having the meaning methyl or ethyl.

Furthermore preferred lactams (IV) and lactam derivatives (II) and (III) as starting materials for the inventive process are those in which the fonnula part

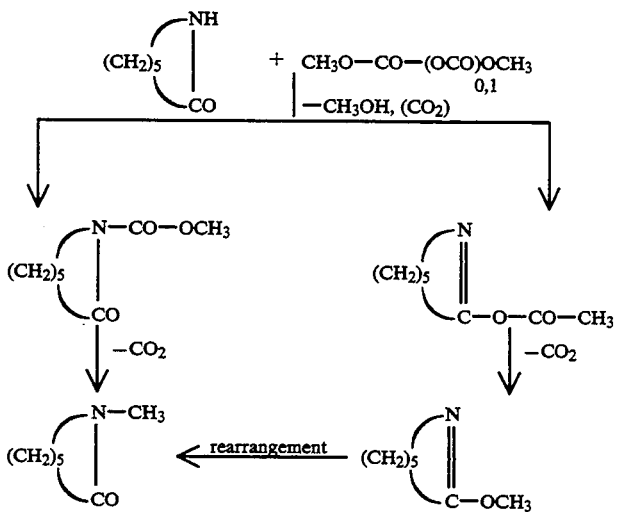

From this representation, it is recognisable that the carbonate or pyrocarbonate employed in the preferred process variant is not an alkylating agent but an acylating agent, and thus differs from dimethyl sulphate, alkyl halides or alcohols. Under the conditions of the preferred variant of the process according to the invention, however, the lactam N- and O-carboxylates intermedi-

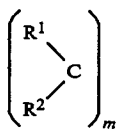

represents a carbon chain with 2 or 3 conjugated C—C-double bonds, the 1,8-naphthylene radical, the 2,2'-biphenylene radical, the o-phenylene-ethylene radical or the o-phenylene-vinylene radical.

Lactams which are suitable for the process according to the invention in its preferred variant are, for example: β-propiolactam, 2- and 3-phenyl-β-propiolactam, 2- and 3-methyl-β-propiolactam, 3-ethyl-β-propiolactam, 3-benzyl-β-propiolactam, 3,3-dimethyl-β-propiolactam, γ-butyrolactam, 4,4-dimethyl-γ-butyrolactam, δ-valerolactam, ε-caprolactam, 2-chloro-caprolactam, 2-, 3-, 4-, 5- and 6-methyl-caprolactam, 2-, 3-, 4-, 5- and 6-phenylcaprolactam, substituted and non-substituted 7-oenantholactam, 8-capryllactam, 12laurolactam, 2-pyridone, 2-quinolone, 2-dihydroquinolone, 2-octahydroquinolone, phthalimidine, naphthostyril, 2-phenanthridinone, 2-oxo-5,6-benzo-tetrahydroazepine, 2-oxo-6,7-benzo-tetrahydroazepine, 7-oxo-4-methyl-hexahydro-1,1,4-diazepine, 1H-2-oxo-5-ethyl-1,5-diazacyclooctane and 1H-2-oxo-1-aza-cyclooctatriene.

The last-mentioned lactams (from 2-pyridone) can be represented in terms of formulae as follows:

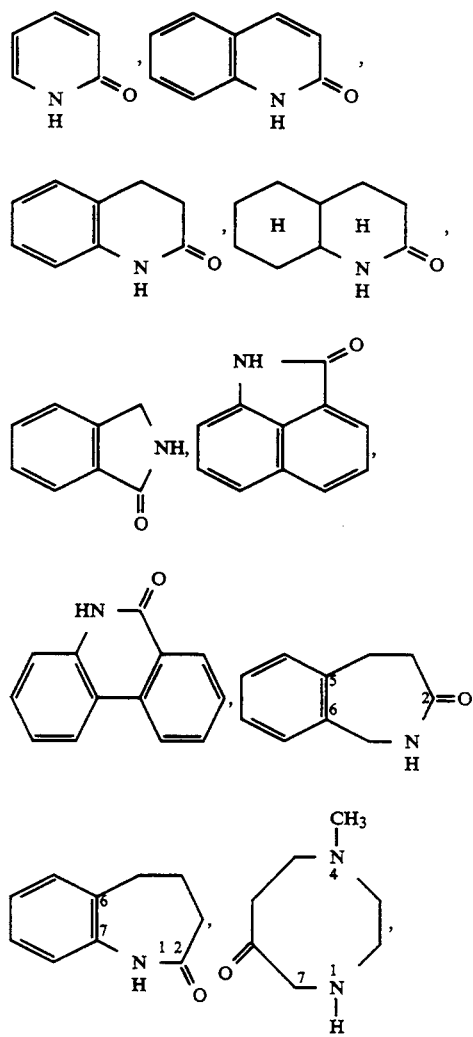

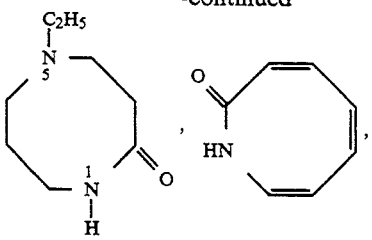

and demonstrate cases in which C ring members in brackets in the formula (I) are replaced by —N(CH₃)— or —N(C₂H₅)—, linked by double bonds or are parts of further rings in the manner mentioned.

Carbonates suitable for use in the preferred variant of the process according to the invention are, for example: dimethyl carbonate, diethyl carbonate, dipropyl carbonate, diisopropyl carbonate, dibutyl carbonate, diisobutyl carbonate, di-sec-butyl carbonate, dipentyl carbonate, dihexyl carbonate, dioctyl carbonate, dicyclohexyl carbonate, diallyl carbonate, dipentenyl carbonate, dibenzyl carbonate and the corresponding pyrocarbonates.

The carbonate or pyrocarbonate of the formula (V) is employed in an amount from 0.5–5 mol, preferably 1–3 mol, particularly preferably 1.2–1.7 mol, per mol of lactam (IV).

The process according to the invention can be carried out in the presence or in the absence of an inert solvent. Such solvents are, for example, (halogeno)hydrocarbons, such as hexane, cyclohexane, petroleum ether, ligroin, benzene, toluene, xylene, chlorobenzene, dichlorobenzene, naphthalene or decalin, or alcohols, such as methanol, ethanol, (iso)propanol and (iso)-butanol, esters, such as ethyl acetate and butyl acetate, N-persubstituted amides, such as dimethylformamide and dimethylacetamide, N-methyl-pyrrolidone (NMP) and N-methyl-caprolactam (NMC) and others which are inert under the conditions of the process according to the invention. Solvents are in particular employed if the starting compounds to be reacted are higher melting or if, for example, the process is to be carried out in the downward-flow phase or the liquid phase.

The process according to the invention can furthermore be carried out in the presence or in the absence of catalysts having acidic and/or basic centers. The presence of such catalysts as a rule enables the reaction temperature to be lowered within the range indicated and thus the total reaction mixture to be protected from thermal overloading.

Catalysts having acidic or mainly acidic centres are known to the person skilled in the art. They include various classes of substance, for example the clay minerals, such as kaolinires, bentonires, montmorillonites or attapulgites;

the carriers containing acids or free acids or acid groups, such as hydrochloric acid, nitric acid, sulphuric acid, phosphoric acid, oxalic acid, acetic acid, trifluoroacetic acid, benzenesulphonic acid or toluenesulphonic acid, cation exchanger resins in the H⁺ form or active carbon, SiO₂, Al₂O₃ or clay minerals which are impregnated with the acids mentioned;

the group of predominantly acid-reacting metal oxides and metal sulphides, such as zinc oxide, cadmium oxide, aluminium oxide, cerium oxide, thorium oxide, titanium oxide, zirconium oxide, tin oxide, niobium oxide, tantalum oxide, lead oxide, arsenic oxide, bismuth oxide, antimony oxide, vanadium oxide, chromium oxide, molybdenum oxide, tungsten oxide cadmium sulphide and zinc sulphide;

the group of metal salts, such as $MgSO_4$, $CaSO_4$, $SrSO_4$, $BaSO_4$, $CuSO_4$, $ZnSO_4$, $CdSO_4$, $Al_2(SO_4)_3$, $FeSO_4$, $Fe_2(SO_4)_3$, $CoSO_4$, $NiSO_4$, $Cr_2(SO_4)_3$, $KHSO_4$, $K_2SO_4$, $(NH_4)_2SO_4$, $Zn(NO_3)_2$, $Ca(NO_3)_2$, $Bi(NO_3)_3$, $Fe(NO_3)_3$, $CaCO_3$, $BPO_4$, $AlPO_4$, $CrPO_4$, $Cu_3(PO_4)_2$, $Zn_3(PO_4)_2$, $Mg_3(PO_4)_2$, $Ti_3(PO_4)_4$, $Zr_3(PO_4)_4$, $Ni_3(PO_4)_2$, $AgCl$, $CuCl_2$, $CuCl$, $CaCl_2$, $AlCl_3$, $TiCl_3$, $SnCl_2$, $CaF_2$, $BaF_2$, $Al(ClO_4)_3$, $Mg(ClO_4)_2$ and others as well as mixtures of several of the salts mentioned;

the group of mixed oxides, which can also be employed in various mixture ratios of several of them, such as $SiO_2$-$Al_2O_3$, $SiO_2$-$TiO_2$, $SiO_2$-$SnO_2$, $SiO_2$-$ZrO_2$, $SiO_2$-$BeO$, $SiO_2$-$MgO$, $SiO_2$-$CaO$, $SiO_2$-$SrO$, $SiO_2$-$BaO$, $SiO_2$-$ZnO$, $SiO_2$-$Ga_2O_3$, $SiO_2$-$Y_2O_3$, $SiO_2$-$La_2O_3$, $SiO_2$-$MoO_3$, $SiO_2$-$WO_3$, $SiO_2$-$V_2)_5$, $SiO_2$-$ThO_2$, $Al_2O_3$-$MgO$, $Al_2O_3$-$ZnO$, $Al_2O_3$-$CdO$, $Al_2O_3$-$B_2O_3$, $Al_2O_3$-$ThO_2$, $Al_2O_3$-$TiO_2$, $Al_2O_3$-$ZrO_2$, $Al_2O_3$-$V_2O_5$, $Al_2O_3$-$MoO_3$, $Al_2O_3$-$WO_3$, $Al_2O_3$-$Cr_2O_3$, $Al_2O_3$-$Mn_2O_3$, $Al_2O_3$-$Fe_2O_3$, $Al_2O_3$-$Co_3O_4$, $Al_2O_3$-$NiO$, $TiO_2$-$CuO$, $TiO_2$-$MgO$, $TiO_2$-$ZnO$, $TiO_2$-$CdO$, $TiO_2$-$ZrO_2$, $TiO_2$-$SnO_2$, $TiO_2$-$Bi_2O_3$, $TiO_2$-$Sb_2O_5$, $TiO_2$-$V_2O_5$, $TiO_2$-$Cr_2O_3$, $TiO_2$-$MoO_3$, $TiO_2$-$WO_3$, $TiO_2$-$Fe_2O_3$, $TiO_2$-$Mn_2O_3$, $TiO_2$-$Co_3O_4$, $TiO_2$-$NiO$, $ZrO_2$-$CdO$, $ZnO$-$MgO$, $ZnO$-$Fe_2O_3$, $MoO_3$-$CoO$-$Al_2O_3$, $MoO_3$-$NiO$-$Al_2O_3$, $TiO_2$-$SiO_2$-$MgO$, $MoO_3$-$Al_2O_3$-$MgO$, heteropolyacids and others;

the group of so-called solid super acids, such as $SbF_5$ or $TaF_5$ and others on carriers such as $SiO_2$, $Al_2O_3$, $SiO_2$-$Al_2O_3$, $SiO_2$-$TiO_2$, $SiO_2$-$ZrO_2$, $TiO_2$-$ZrO_2$, $MoO_3$, $ThO_2$-$Cr_2O_3$, $Al_2O_3$-$WO_3$ and others;

the group of zeolites, such as X, Y, mordenite, L, ZSM5, [B]ZSM5, [Fe]ZSM5, [Ti]ZSM5, [Ga]ZSM5, [Cr]ZSM5, ZSM11, EU1, ZSM48, ZSM12, ZSM22, ZSM23, erionite, offretite, mazzite, chabasite, PSH3, $\beta$; the microporous crystalline zeolite analogues, such as ALPOs, SAPOs and MeAPOs, and others, which in the H form, but also in the form exchanged with metal cations, as is known to the person skilled in the art, furthermore have acidic centers, in particular with Mg, Ca, Zn, Cu, Sn and rare earths, but also with K, Rb, Cs, Sr and Ba, in which the basic character increases.

Catalysts having a mainly basic disposition, which are suitable for the reaction according to the invention, are, for example, metal hydroxides, oxides, alkoxides and hydrides, of the alkali metal or alkaline earth metal series, for example, LiOH, NaOH, KOH, St(OH)$_2$, Ba(OH)$_2$, Na$_2$O, CaO, SrO, BaO, NaOCH$_3$, NaOC$_2$H$_5$, KOC$_4$H$_9$, NaH, alkali metal and alkaline earth metal carbonates or hydrogen carbonates, such as $Li_2CO_3$, $Na_2CO_3$, $NaHCO_3$, $K_2CO_3$, $KHCO_3$, $Cs_2CO_3$, $MgCO_3$, $CaCO_3$, $SrCO_3$ and $BaCO_3$.

The process according to the invention can be carried out either in the liquid phase or in the gas phase or downward-flow phase. The reaction here can be carried out under normal pressure, reduced pressure or elevated pressure. Working in the liquid phase, for example in an autoclave is suitable here for batchwise reaction mixtures, while the gas phase or the downward-flow phase are mainly suitable for continuous processes on the industrial scale. The liquid phase is used in the reaction of poorly vaporisable starting substances or high-boiling (pyro)carbonates, it being possible in the case of slightly reactive starting substances to set a higher reaction temperature for accelerating the reaction by increasing the pressure. With easily vaporisable starting substances, in many cases the industrially favourable gas phase reaction is selected.

The process according to the invention can be carried out in a wide temperature range from 80° to 450° C. For carrying out in the gas phase, the process is preferably carried out in the upper part of this range and for carrying out in the liquid phase it is preferably carried out in the lower part of this range. For the gas phase, therefore, a range from 250° to 400° C., particularly preferably from 300° to 350° C., may preferably be mentioned. For the liquid phase, including the downward-flow phase and if appropriate under elevated pressure, a range from 80° to 300° C., particularly preferably a range from 80° to 250° C., very particularly preferably a range from 100° to 200° C., may therefore be mentioned.

Thus, for example, a mixture of the lactam (IV), the carbonate or pyrocarbonate (V) and optionally a solvent and optionally a catalyst are brought into a reactor and brought to reaction temperature therein under normal pressure or at elevated pressure (in an autoclave) and reacted at this temperature. When working in an autoclave, in this case the process can preferably be carried out under the pressure ($CO_2$) automatically established.

In another form of carrying out the process, the lactam (IV) and the carbonate or pyrocarbonate (V), metering taking place as a mixture or in separate substance streams, are led through a flow reactor, in which inert packings or packings consisting of one or more of the catalysts mentioned which have acidic and/or basic centres (optionally mixtures of inert packings and catalysts) are arranged. This arrangement in the flow reactor can be present as a solid bed, as a fluid bed or as a fluidised layer. For this procedure, the substances (IV) and (V) to be reacted are converted to the gas phase. This conversion to the gas phase can also be performed upstream of the reactor in a pre-evaporator. In this form of carrying out the process, the reaction components (IV) and (V) to be reacted can also be employed separately or together as a solution in one of the solvents mentioned; the vapour of the solvent formed is then used in the liquid phase for better metering and in the gas phase as a carrier.

In a still further variant of carrying out the reaction, the substances (IV) and (V) to be reacted, converted into the gas form, are passed, optionally together with a solvent, over the catalyst in a solid bed, which catalyst is additionally coated with a stationary liquid phase, for example polyethylene glycol (gas-liquid phase transfer catalysis).

In a still further form of carrying out the process, inert packings, catalysts having acidic and/or basic centres or mixtures of inert packings and catalysts having active centres can be placed as a solid bed in a flow reactor and the mixture of (IV) and (V) to be reacted can be passed over it in the liquid phase (downward-flow phase process). In this form of carrying out the process too, a solvent can additionally be employed.

In the case in which the process is carried out in a flow reactor in the gas phase or in the downward-flow phase, catalyst loadings (expressed in grams of starting substances (IV) and (V) per gram of catalyst per hour)

of 0.1–5 g/g/h, preferably 0.25–2 g/g/h, particularly preferably 0.5–1 g/g/h, are set.

EXAMPLES

List of the catalysts employed in the Examples:

| No. | Type (Manufacturer) | Modulus | Binder |
|---|---|---|---|
| 1) | H-ZSM 5 | 180 | 30% $Al_2O_3$ |
| 2) | H/Cu-ZSM 5 | 70 | 30% $Al_2O_3$ 4.7% CuO |
| 3) | Sn-ZSM 5 | 90 | 15% $SiO_2$ |
| 4) | H-mordenite | 13 | 30% $Al_2O_3$ |
| 5) | H-EU1 | 31 | 30% $Al_2O_3$ |
| 6) | H-ZSM 12 | 183 | 30% $Al_2O_3$ |
| 7) | H-$\beta$ | 15 | 30% $Al_2O_3$ |
| 8) | H-Y | 4.7 | 30% $Al_2O_3$ |
| 9) | SE-Y | 4.7 | 30% $Al_2O_3$ (0.3 mol of $La_2O_3$) |
| 10) | Mg-Y | 4.8 | 15% $SiO_2$ |
| 11) | Ca-Y | 4.6 | 30% $Al_2O_3$ |
| 12) | Na/K-erionite | 6 | 30% $Al_2O_3$ |
| 13) | Cs-X | 2.5 | 15% $SiO_2$ |
| 14) | Mg-X | 2.5 | 30% $Al_2O_3$ |
| 15) | Sr-X | 2.5 | 15% $SiO_2$ |
| 16) | Ba-X | 2.5 | 15% $SiO_2$ |
| 17) | La-X | 2.5 | 15% $SiO_2$ |
| 18) | H-SAPO 5 | — | 30% $Al_2O_3$ |
| 19) | H-SAPO 11 | — | 30% $Al_2O_3$ |
| 20) | ALPO 5 | — | — |
| 21) | ALPO 11 | — | — |
| 22) | BaO | — | — |
| 23) | Niobic acid | — | — |
| 24) | Silica alumina (Condea) | | 5% $SiO_2$/95% $Al_2O_3$ |

| No. | Type (manufacturer) | |
|---|---|---|
| 25) | Al silicate/$H_3PO_4$ | 35 g/l |
| 26) | $\gamma$-$Al_2O_3$ alumina spheres (Condea) | |
| 27) | $\gamma$-$Al_2O_3$ disp. spec. 10/1 (Condea) | 2% HCl |
| 28) | $\gamma$-$Al_2O_3$ disp. spec. 10/1 (Condea) | 0.5% HCl |
| 29) | $\gamma$-$Al_2O_3$ disp. spec. 10/1 (Condea) | untreated |
| 30) | $\gamma$-$Al_2O_3$ Pural SCF (Condea) | 0.35% Na |
| 31) | $\gamma$-$Al_2O_3$ (alkylating contact catalyst) (Condea) | HCl-treated |
| 32) | $\gamma$-$Al_2O_3$ (BASF) D10-10 | |
| 33) | $\gamma$-$Al_2O_3$ (UCI) T2432 | |
| 34) | $\gamma$-$Al_2O_3$ (Rhone Poulenc) SCS 250 | |
| 35) | $\gamma$-$Al_2O_3$ Monal 300 | |
| 36) | $\gamma$-$Al_2O_3$ (Rhone Poulenc) SCS 350 | |
| 37) | $\gamma$-$Al_2O_3$ (Condea) Purol SCF | |
| 38) | $\gamma$-$Al_2O_3$/Ni | |
| 39) | $\gamma$-$Al_2O_3$/Zr | 40 g/l |
| 40) | $\gamma$-$Al_2O_3$/Nb oxalate | 2 g/l |
| 41) | $\gamma$-$Al_2O_3$/Cu/Cr | |
| 42) | $\gamma$-$Al_2O_3$(activated alumina) (Rhone Poulenc) | $NH_4F$-treated |

EXAMPLES 1–32

4 glass tubes of 250 mm length and 12 mm $\phi$ were packed with glass beads of 3 mm $\phi$ and—in the middle of the tube—6 ml of catalyst as granules and heated—arranged vertically—in a gas chromatography oven. While passing nitrogen through (0.6 l/h), the packing was calcined at 400° C. for 3 h, then a solution of 1 mol of caprolactam in 4 mol of dimethyl carbonate was metered into the 350° C. evaporator zone at a feed rate of 3 ml/h. The reaction temperature was 300° C. and the feed rate of the carrier gas 0.6 l of $N_2$/h. The reaction mixture emerging at the lower end of the tube was condensed in cold traps and subjected to gas chromatographic determination.

The results for Examples 1–32 are collated in Table 1.

TABLE 1

| Example | Catalyst | Conversion [%], relative to caprolactam | Selectivity [%] for N-methylcaproplactam |
|---|---|---|---|
| 1 | 1 | 90.0 | 90.0 |
| 2 | 2 | 70.0 | 94.3 |
| 3 | 3 | 90.5 | 95.4 |
| 4 | 4 | 61.3 | 96.0 |
| 5 | 5 | 71.7 | 88.3 |
| 6 | 6 | 91.0 | 96.9 |
| 7 | 7 | 93.6 | 95.6 |
| 8 | 8 | 98.1 | 92.5 |
| 9 | 9 | 93.0 | 95.2 |
| 10 | 10 | 98.1 | 83.3 |
| 11 | 11 | 89.4 | 97.2 |
| 12 | 12 | 71.4 | 98.0 |
| 13 | 13 | 99.5 | 87.5 |
| 14 | 14 | 98.7 | 91.8 |
| 15 | 15 | 99.9 | 87.6 |
| 16 | 16 | 99.6 | 93.1 |
| 17 | 17 | 99.8 | 90.3 |
| 18 | 18 | 96.7 | 94.9 |
| 19 | 19 | 97.3 | 96.0 |
| 20 | 22 | 97.5 | 92.0 |
| 21 | 23 | 87.7 | 95.1 |
| 22 | 24 | 97.4 | 93.3 |
| 23 | 25 | 92.8 | 90.9 (350° C.!) |
| 24 | 26 | 95.5 | 99.2 |
| 25 | 32 | 98.4 | 97.4 |
| 26 | 33 | 87.4 | 97.8 |
| 27 | 34 | 97.1 | 97.5 |
| 28 | 38 | 91.1 | 92.1 |
| 29 | 39 | 95.2 | 98.5 |
| 30 | 40 | 94.4 | 98.5 |
| 31 | 41 | 78.5 | 89.1 |
| 32 | 42 | 76.9 | 64.8 |

EXAMPLES 33–36

In an experimental arrangement as in Examples 1–19, the type of catalyst and the reaction temperatures were varied with the same catalyst and product flow rate of caprolactam and DMC.

The findings of the gas chromatographic investigations can be seen from Table 2.

TABLE 2

| Cat. | Example | Temperature [C.] | Conversion [%], relative to caprolactam | Selectivity [%] for N-methyl-caprolactam |
|---|---|---|---|---|
| 27 | 33 A | 200 | 99.2 | 96.4 |
| | B | 250 | 93.2 | 98.7 |
| | C | 300 | 97.9 | 98.0 |
| | D | 325 | 99.4 | 98.5 |
| | E | 350 | 99.8 | 94.3 |
| 28 | 34 A | 200 | 67.8 | 91.7 |
| | B | 250 | 83.8 | 98.6 |
| | C | 300 | 93.8 | 99.1 |
| | D | 325 | 96.9 | 98.4 |
| | E | 350 | 97.8 | 94.9 |
| 29 | 35 A | 200 | 75.2 | 84.9 |
| | B | 250 | 80.9 | 97.6 |
| | C | 300 | 98.4 | 99.5 |
| | D | 325 | 96.8 | 98.4 |
| | E | 350 | 99.1 | 94.4 |
| 30 | 36 A | 200 | 99.3 | 92.3 |
| | B | 250 | 94.9 | 98.2 |
| | C | 300 | 98.6 | 99.5 |
| | D | 325 | 99.3 | 99.3 |
| | E | 350 | 99.7 | 95.1 |

EXAMPLES 37–41

In the same experimental arrangement as in Examples 1–32, 3 ml/h of a solution of caprolactam and dimethyl carbonate in a solvent were brought to reaction on the catalyst using 6 ml of catalyst 27 in each case. Table 3 gives details of the results when using different mixture proportions of caprolactam/dimethyl carbonate/solvent and reaction temperatures.

TABLE 3

| Example | Reaction temp. [°C.] | Solvent [% by weight] | Molar ratio caprolactam/DMC | Conversion, based on caprolactam | Selectivity for NMC |
|---|---|---|---|---|---|
| 37 A | 300 | Benzene (60) | 1:1.2 | 89.5 | 99.7 |
| B | 350 | Benzene (60) | 1:1.2 | 99.5 | 97.6 |
| 38 A | 300 | Benzene (60) | 1:1.5 | 92.0 | 99.1 |
| B | 350 | Benzene (60) | 1:1.5 | 99.4 | 97.1 |
| 39 A | 300 | Methanol (33.3) | 1:1 | 62.2 | 98.7 |
| B | 350 | Methanol (33.3) | 1:1 | 92.5 | 99.3 |
| 40 A | 300 | Methanol (20) | 1:1.5 | 67.2 | 98.2 |
| B | 350 | Methanol (20) | 1:1.5 | 96.2 | 97.1 |
| 41 A | 300 | NMC (33.3) | 1:1.2 | 65.0 | 99.8 |
| B | 350 | NMC (33.3) | 1:1.2 | 92.0 | 99.6 |

EXAMPLES 42

In an oil-heated glass tube reactor of 30 cm length and 5 cm $\phi$, 30 g of catalyst 31, embedded in the middle of a packing of glass beads of 5 mm $\phi$, were calcined at 340° C. for 3 h in a 6 l/h stream of nitrogen. At the same time, 7.55 g (0,067 mol)/h of caprolactam from a melt kept at 90° C. and 9.0 g (0.1 mol)/h of dimethyl carbonate were then metered into the evaporater zone above the contact catalyst and passed over the contact catalyst kept at 325° C. after evaporation of the mixture together with 6 l/h of $N_2$ as a carrier gas. The reaction mixture collected in a cold trap as condensate was subjected to gas chromatographic investigation. After 1 h, the conversion, based on caprolactam, was 95% and the selectivity for N-methylcaprolactam 97%.

EXAMPLES 43–50

With the same procedure as in Example 42, 15 g/h of a mixture of caprolactam and dimethyl carbonate kept in solution at 40° C. was metered into the evaporator zone in the molar ratio 1:1.5 and passed over the catalyst (30 g) at reaction temperature with $N_2$ as the carrier gas (6 l/h). Conversions, based on caprolactam, and the selectivity for N-methylcaprolactam follow from Table 4:

TABLE 4

| Example | Catalyst | Temp. [°C.] | Conversion [%] | Selectivity [%] |
|---|---|---|---|---|
| 43 | 31 | 325 | 95.7 | 98.7 |
| 44 | 18 | 345 | 90.5 | 98.3 |
| 45 | 19 | 345 | 93.5 | 97.8 |
| 46 | 20 | 345 | 98.2 | 93.6 |
| 47 | 21 | 345 | 98.5 | 93.4 |
| 48 | 35 | 345 | 98.8 | 98.2 |
| 49 | 36 | 345 | 97.5 | 95.1 |
| 50 | 37 | 345 | 99.4 | 95.2 |

EXAMPLES 51–54

In a procedure analogous to Examples 1–32, methyl lactam N-carboxylate in 33.3% strength solution in benzene was metered into the 350° C. evaporation zone at a delivery rate of 3 ml/h and passed over 6 ml of various catalysts with 0.6 l/h of $N_2$ as a carrier gas. The reaction temperature was 350° C. The results of the gas chromatographic determination are collated in Table 5.

TABLE 5

| Example | Catalyst | Conversion [%] lactam carboxylate | Selectivity [%] for N-methylcaprolactam |
|---|---|---|---|
| 51 | 1 | 100 | 72.3 |
| 52 | 9 | 100 | 70.5 |
| 53 | 19 | 100 | 81.9 |
| 54 | 27 | 100 | 86.8 |

EXAMPLES 55–58

Analogously to Examples 1–32, a mixture of pyrrolidone and dimethyl carbonate in the molar ratio 1:1.5 was reacted on 6 ml samples of various catalysts with a delivery rate of 3 ml/h. Reaction temperatures, catalysts and yield results are recorded in Table 6.

TABLE 6

| Example | Catalyst | Reaction temp. [°C.] | Conversion [%] based on pyrrolidone | Selectivity [%] for N-methyl-pyrrolidone |
|---|---|---|---|---|
| 55 A | 27 | 300 | 99.1 | 99.1 |
| B | 27 | 350 | 99.8 | 98.6 |
| 56 A | 28 | 300 | 94.5 | 98.9 |
| B | 28 | 350 | 99.9 | 98.4 |
| 57 A | 29 | 300 | 92.0 | 99.0 |
| B | 29 | 350 | 99.9 | 98.3 |
| 58 A | 30 | 300 | 100 | 98.0 |
| B | 30 | 350 | 99.9 | 98.0 |

EXAMPLES 59–64

Analogously to Examples 1–32, a mixture of caprolactam and diethyl carbonate was employed in the molar ratio 1:4. Reaction data and yield information can be seen from Table 7.

TABLE 7

| Example | Catalyst | Reaction temp. [°C.] | Conversion [%], based on pyrrolidone | Selectivity [%] for N-methyl-pyrrolidone |
|---|---|---|---|---|
| 59 A | 27 | 300 | 77.2 | 98.6 |
| B |  | 350 | 98.3 | 93.1 |
| 60 A | 28 | 300 | 68.9 | 98.6 |
| B |  | 350 | 96.1 | 92.2 |
| 61 A | 29 | 300 | 65.9 | 98.4 |
| B |  | 350 | 97.8 | 90.0 |
| 62 A | 30 | 300 | 86.3 | 98.6 |
| B |  | 350 | 98.7 | 88.8 |
| 63 | 6 | 300 | 65.1 | 78.3 |
| 64 | 7 | 300 | 68.5 | 93.9 |

EXAMPLES 65–68

Analogously to Examples 1–32, a 66.6% strength solution of caprolactam and dipropyl carbonate in benzene was reacted in various catalysts. Reaction data and yield information are collated in Table 8.

TABLE 8

| Example | Catalyst | Reaction temp. [°C.] | Conversion [%] based on pyrrolidone | Selectivity [%] for N-methyl-pyrrolidone |
|---|---|---|---|---|
| 65 A | 27 | 300 | 49.5 | 93.3 |
| B | 27 | 350 | 98.0 | 96.1 |
| 66 A | 28 | 300 | 49.8 | 94.5 |
| B | 28 | 350 | 87.4 | 96.2 |
| 67 A | 29 | 300 | 48.2 | 95.1 |
| B | 29 | 350 | 88.5 | 96.4 |
| 68 A | 30 | 300 | 58.7 | 95.7 |

TABLE 8-continued

| Example | Catalyst | Reaction temp. [°C.] | Conversion [%] based on pyrrolidone | Selectivity [%] for N-methyl-pyrrolidone |
|---|---|---|---|---|
| B | 30 | 350 | 94.1 | 95.4 |

EXAMPLE 69

In a 500 ml autoclave, a mixture of 28.5 g (0.3 mol) of 2-pyridone, 81.1 g (0.9 mol) of dimethyl carbonate and 6g of $K_2CO_3$ was heated to 220° C. under an initial $N_2$ pressure of 10 bar and kept at this temperature for 6 h. After cooling, the mixture was taken up in toluene, the catalyst was filtered off with suction, the organic phase was concentrated and the residue was distilled: yield 29 g (88.6%) of pale oil of b.p. 254°–256° C.; according to GC the purity was 99.9% of N-methyl-2-pyridone.

EXAMPLE 70

A mixture of 14.3 g (0.15 mol) of 2-pyridone, 40.5 g (0.45 mol) of DMC and 2 g of $K_2CO_3$ was heated under reflux (94°→83° C.) for 24 h. The GC investigation of the reaction mixture showed 100% conversion and 99.0% selectivity for N-methyl-2-pyridone.

EXAMPLE 71

33.8 g (0.2 mol) of naphtholactam, 70.9 g (0.6 mol) of diethyl carbonate and 5 g of $K_2CO_3$ powder were adjusted in a 250 ml autoclave with $N_2$ to an initial value of 10 bar, heated to 250° C. and kept at this temperature for 6 h (84 bar). According to GC, the conversion was 97.9%, the selectivity for N-ethyl-naphtholactam 99%.

EXAMPLE 72

With the same procedure as in Example 71, after 6 (12) h and 200° C. the conversion was 71.7% (97.4%) and the selectivity for N-ethyl-naphtholactam 99%.

EXAMPLE 73

If the starting materials according to Example 71 were reacted under reflux conditions (125° C.) at normal pressure, a 99% selectivity for N-ethyl-naphtholactam was obtained after 40 h with a conversion of 80%.

EXAMPLE 74

1 g ($10^{-3}$ mol) of phenanthridinone, 9 g (0.1 mol) of dimethyl carbonate and 0.5 g of $K_2CO_3$ powder were reacted with one another under the sane conditions as in Example 71. After 6 h at 220° C., the conversion was 99.1% and the selectivity for N-methylphenanthridinone 87%.

What is claimed is:

1. A process for the preparation of a N-substituted lactam of the formula

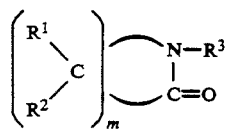

in which
m denotes an integer from 2 to 12,
$R^1$ and $R^2$ independently of one another represent hydrogen, straight-chain or branched $C_1$-$C_6$-alkyl, straight-chain or branched $C_3$-$C_6$-alkenyl, cyclohexyl, benzyl, phenyl, fluorine, chlorine or bromine, two substituents $R^1$ and $R^2$ other than hydrogen being present on the number of C ring members designated by the integer m and wherein one of the C ring members in brackets not adjacent to the carbonyl or nitrogen in the ring can optionally be replaced by —$N(CH_3)$— or —$N(C_2H_5)$—, and wherein several of the C ring members may optionally be lined by double bonds and wherein two or more of the C ring members in brackets together with the $R^1$ and $R^2$ radicals may form an aromatic or cycloaliphatic ring, and $R^3$ denotes straight-chain or branched $C_1$-$C_8$-alkyl, $C_3$-$C_8$-alkenyl, or cycloalkyl wherein a lactam N-carboxylate or lactim O-carboxylate of the formulae

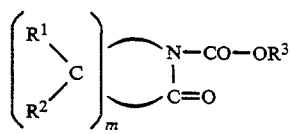

or

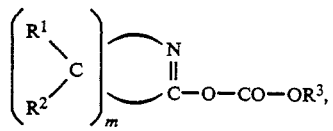

in which m, $R^1$, $R^2$, and $R^3$ have the above meaning, are cleaved, with elimination of $CO_2$, at temperatures of 80° to 450° C. in the gas or the liquid phase, in the case of the use of a lactim O-carboxylate the intermediately formed lactim ether being rearranged under the reaction conditions to the N-substituted lacatam.

2. The process of claim 1, wherein the lactam N-carboxylate and lactim O-carboxylate, respectively, to be employed are prepared in situ by reaction of a lactam of the formula

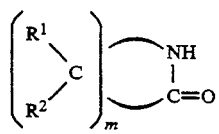

with a carbonate or pyrocarbonate of the formula

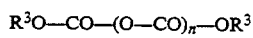

in which
m denotes an integer from 2 to 12 and
n denotes 0 or 1,
$R^1$, $R^2$ and $R^3$ have the meaning given in claim 16 at temperatures of 80°–450° C., and are converted into the N-substituted lactams under the same conditions and with $CO_2$ elimination without intermediate isolation.

3. The process of claim 1, wherein m denotes the number 3, 4, 5 or 12.

4. The process of claim 1, wherein $R^1$ and $R^2$ are replaced by $R^{11}$ and $R^{12}$, where
$R^{11}$ denotes hydrogen, straight-chain or branched $C_1$-$C_4$-alkyl, allyl, butenyl, $C_5$-$C_7$-cycloalkyl benzyl, phenyl or chlorine and $R^{12}$ represents hydrogen, straight-chain or branched $C_1$–$C_4$-alkyl or chlorine.

5. The process of claim 4, wherein $R^{11}$ and $R^{12}$ are replaced by $R^{21}$ and $R^{22}$, where $R^{21}$ denotes hydrogen, methyl, ethyl, benzyl or phenyl and $R^{22}$ represents hydrogen, methyl or ethyl, 6. The process of claim 1, wherein the formula part

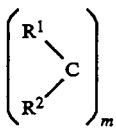

represents a carbon chain with 2 or 3 conjugated C—C-double bonds, the 1,8-naphthylene radical, the 2,2'-biphenylene radical, the o-phenylene-ethylene radical or the o-phenylene-vinylene radical.

7. The process of claim 2, wherein the formula part

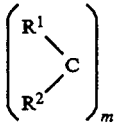

represents a carbon chain with 2 or 3 conjugated C—C-double bonds , the 1,8-naphthylene radical, the 2,2'-biphenylene radical , the o-phenylene-ethylene radical or the o-phenylene-vinylene radical.

8. The process of claim 1, wherein $R^3$ is repaced by $R^{13}$ having the meaning straight chain or branched $C_1$–$C_4$-alkyl, allyl or propargyl.

9. The process of claim 8, wherein $R^{13}$ is replaced by $R^{23}$ having the meaning methyl or ethyl.

10. The process of claim 1, which is carried out in the presence of a catalyst having acidic and/or basic centres, said catalysts being selected from the group comprising the clay minerals, carriers containing acids, free acids or acid groups, acid-reacting metal oxides and metal sulphides, metal salts, mixed oxides, solid superacids, acidic zeolites and zeolites exchanged with metal cations, and the hydroxides, oxides, alkoholates, hydrides, bicarbonates and carbonates of the alkali(ne earth) metals.

11. The process of claim 1, which is carried out in the gas phase in a temperature range from 250° to 400° C.

12. The process of claim 11, which is carried out at 300° to 350° C.

13. The process of claim 1, which is carried out in the liquid phase in a temperature range from 80° to 300° C.

14. The process of claim 13, which is carried out at 80° to 250° C.

15. The process of claim 14, which is carried out at 100° to 200° C.

16. The process of claim 1, wherein the N-substituted lactam is selected from the group consisting of β-propiolactam, 2- and 3-phenyl-β-propiolactam, 2- and 3-methyl-β-propiolactam, 3-ethyl-β-propiolactam, 3-benzyl-β-propiolactam, 3,3-dimethyl-β-propiolactam, γ-butyrolactam, 4,4-dimethyl-γ-butyrolactam, δ-valerolactam, ε-caprolactam, 2-chloro-caprolactam, 2-, 3-, 4-, 5- and 6-methyl caprolactam, 2-, 3-, 4-, 5- and 6-phenylcaprolactam, substituted and non-substituted 7-oenantholactam, 8-capryllactam, 12-laurolactam, 2-pyridone, 2-quinolone, 2-dihydroquinolone, 2-octahydroquinolone, phthalimidine, naphthostyril, 2-phenanthridinone, 2-oxo-5,6-benzo-tetrahydroazepine, 2-oxo-6,7-benzo-tetrahydroazepine, 7-oxo-4-methyl-hexahydro-1,4-diazepine, 1H-2-oxo-5-ethyl-1,5-diazacyclooctane and 1H-2-oxo-1-aza-cyclooctatriene.

* * * * *

UNITED STATES PATENT AND TRADEMARK OFFICE
CERTIFICATE OF CORRECTION

PATENT NO : 5,338,861
DATED : August 16, 1994
INVENTOR(S) : Artur BOTTA, et al.

It is certified that error appears in the above-identified patent and that said Letters Patent are hereby corrected as shown below:

Column 14, line 8, cancel "lined" and substitute --linked--

Signed and Sealed this

Twenty-first Day of September, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO : 5,338,861
DATED : August 16, 1994
INVENTOR(S): Artur BOTTA, et al.

It is certified that error appears in the above-identified patent and that said Letters Patent is hereby corrected as shown below:

Column 15, line 37, cancel  "repaced" and substitute --replaced--

Signed and Sealed this

Twenty-sixth Day of October, 1999

*Attest:*

Q. TODD DICKINSON

*Attesting Officer*  *Acting Commissioner of Patents and Trademarks*